(12) United States Patent
Hoke, II et al.

(10) Patent No.: US 9,072,671 B2
(45) Date of Patent: *Jul. 7, 2015

(54) PROCESS FOR ORAL CARE MATERIAL TASTE AND/OR ODOR IMPROVEMENT

(71) Applicant: The Procter & Gamble Company, Cincinnati, OH (US)

(72) Inventors: Steven Hamilton Hoke, II, West Chester, OH (US); John Christian Haught, West Chester, OH (US); Qingxin Lei, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/756,836

(22) Filed: Feb. 1, 2013

(65) Prior Publication Data

US 2014/0037555 A1 Feb. 6, 2014

Related U.S. Application Data

(60) Provisional application No. 61/678,942, filed on Aug. 2, 2012.

(51) Int. Cl.
| | |
|---|---|
| *A61Q 11/00* | (2006.01) |
| *A61K 31/12* | (2006.01) |
| *A61K 31/11* | (2006.01) |
| *A61K 31/16* | (2006.01) |
| *A61K 31/13* | (2006.01) |
| *A61K 31/075* | (2006.01) |
| *A61K 8/18* | (2006.01) |
| *A61K 8/21* | (2006.01) |
| *A61K 8/31* | (2006.01) |
| *A61K 8/55* | (2006.01) |
| *A61K 8/58* | (2006.01) |
| *A61K 8/25* | (2006.01) |
| *A61K 8/37* | (2006.01) |
| *A61K 8/60* | (2006.01) |
| *A61K 8/91* | (2006.01) |
| *A61K 8/02* | (2006.01) |
| *B01D 11/02* | (2006.01) |

(52) U.S. Cl.
CPC . *A61K 8/18* (2013.01); *A61K 31/12* (2013.01); *A61K 31/13* (2013.01); *A61K 31/075* (2013.01); *A61K 31/11* (2013.01); *A61K 31/16* (2013.01); *A61K 8/21* (2013.01); *A61K 8/31* (2013.01); *A61K 8/55* (2013.01); *A61K 8/58* (2013.01); *A61Q 11/00* (2013.01); *A61K 8/25* (2013.01); *A61K 8/37* (2013.01); *A61K 8/60* (2013.01); *A61K 8/91* (2013.01); *A61K 8/0216* (2013.01); *A61K 2800/80* (2013.01); *B01D 11/0288* (2013.01)

(58) Field of Classification Search
CPC ............. A61K 8/18; A61K 8/21; A61K 8/58; A61K 8/55; A61K 8/31; A61K 31/12; A61K 31/11; A61K 31/16; A61K 31/13; A61K 31/075; A61Q 11/00
USPC .......................................................... 424/49
See application file for complete search history.

(56) References Cited

U.S. PATENT DOCUMENTS

| | | | |
|---|---|---|---|
| 3,988,344 | A | 10/1976 | Nakaoji |
| 4,352,829 | A | 10/1982 | Noyes et al. |
| 4,818,533 | A | 4/1989 | Boulware et al. |
| 5,322,643 | A | 6/1994 | Schwartz et al. |
| 5,807,816 | A | 9/1998 | Cottrell et al. |
| 2002/0010104 | A1 | 1/2002 | Ewbank et al. |
| 2007/0123445 | A1 | 5/2007 | Tuzi et al. |
| 2010/0069477 | A1 | 3/2010 | Itoh et al. |
| 2012/0121777 | A1 * | 5/2012 | Wehrli .......................... 426/330 |

FOREIGN PATENT DOCUMENTS

| | | | |
|---|---|---|---|
| CA | 218510 | A1 * | 3/1998 |
| FR | 2 733 982 | A1 | 11/1996 |
| WO | WO94/09108 | A1 | 4/1994 |

(Continued)

OTHER PUBLICATIONS

U.S. Appl. No. 13/564,823, filed Aug. 2, 2012, Hoke II et al.
U.S. Appl. No. 13/564,841, filed Aug. 2, 2012, Hoke II et al.
U.S. Appl. No. 13/564,853, filed Aug. 2, 2012, Hoke II et al.
International Search Report for PCT/US2012/049332, dated Nov. 22, 2012.
International Search Report for PCT/US2012/049314, dated Dec. 10, 2012.
International Search Report and Written Opinion for—PCT/US2013/024357 dated Oct. 27, 2014.
PCT International Search Report dated Nov. 25, 2014—12 pages.

*Primary Examiner* — Frederick Krass
*Assistant Examiner* — Tracy Liu
(74) *Attorney, Agent, or Firm* — Amanda T. Barry

(57) ABSTRACT

Processes for improving the taste of oral care raw materials using solvent extraction, said process comprising the steps of: providing a solid oral care raw material composition in need of treatment wherein said oral care raw material composition comprises an orally acceptable raw material and one or more undesirable non-polar materials; contacting said oral care raw material composition with an extraction solvent to form an extraction mixture comprising a solid phase and a solvent phase; and separating the solid phase from the extraction mixture; wherein the extraction solvent is selected from solvents having individual Hansen solubility parameters of a dispersion force component ($\delta_D$) ranging from about 15 to about 17 (MPa)$^{0.5}$, a polar component ($\delta_P$) ranging from 0 to about 9 (MPa)$^{0.5}$ and a hydrogen bonding component ($\delta_H$) ranging from 0 to about 11 (MPa)$^{0.5}$.

17 Claims, No Drawings

(56) References Cited

FOREIGN PATENT DOCUMENTS

| WO | WO 98/26036 A1 | 6/1998 |
| WO | WO 00/06690 A1 | 2/2000 |
| WO | WO 02/092028 A2 | 11/2002 |
| WO | WO 2008/005550 A2 | 1/2008 |
| WO | WO 2011046423 A1 * | 4/2011 |

* cited by examiner

PROCESS FOR ORAL CARE MATERIAL TASTE AND/OR ODOR IMPROVEMENT

FIELD OF THE INVENTION

The present invention relates to oral care raw material compositions containing undesirable non-polar materials and liquid extraction processes for improving the taste and/or odor of such compositions.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual or perceived efficacy. Since many efficacious oral care components have undesirable taste, color, odor or clarity, efforts to improve these characteristics are common in the art. For taste, one way to remedy an undesirable product taste is to add additional components, such as flavors, that will improve the overall taste experience for the consumer. However, such remedies can be expensive and it may be difficult to entirely mask an undesirable taste. Improvement of color or clarity through dyes or other additives has similar issues.

Oral care raw materials such as stannous fluoride are commercially available for use in a variety of consumer products, including oral care compositions. Although these materials are known to provide desirable dental benefits, a formulator wishing to incorporate these materials into an oral care product, such as a dentifrice, have to overcome the negative taste profile commonly associated with commercially available metal salts like stannous fluoride. Although taste may not be a consideration in other consumer product industries, such as laundry, shampoo or personal cleansing, it is an important consideration in oral care. Similarly, while any undesirable odor associated with materials used in laundry, shampoo or personal cleansing products can typically be remedied by the addition of perfume, perfume levels must be kept to a minimum in oral care compositions for consumer acceptance and could produce further unpleasant tastes when utilized.

Purification of materials through steam-stripping, vacuum-stripping, and/or carbon filtration processes is also generally known to beneficially remove impurities to increase efficacy, minimize undesirable side reactions, and the like. However, these purification processes have been found to be insufficient to remedy the unpleasant tastes and/or odors associated with commercially available oral care raw material materials.

Solvent extractions are generally known in the art as useful for separating components of a mixture, such as wherein the constituents have differing polarities which can be separated when mixed within two immiscible solvents that form a liquid bilayer after mixing. For example, liquid-liquid solvent extractions (LLEs) are useful for purifying or cleaning samples which contain impurities of significantly differing polarity than the majority or desirable component(s) of the sample. This can be achieved by mixing a sample with a solvent that is immiscible with the primary liquid in which the sample is dissolved.

LLE has been utilized in chemical processing to reduce or eliminate undesirable by-products or contaminants. For instance, PCT Patent Application WO 2008005550 to Hoke, et al (Procter & Gamble) discloses a water washing procedure to remove polar sulfur impurities from peppermint oils to avoid malodor formation when formulated in dentifrice containing stannous ions. In U.S. Pat. No. 4,352,829 to Noyes, et al (Procter & Gamble) an ethyl acetate extraction of caffeine from coffee was shown to be an effective decaffeination process.

However, there is still an interest in finding ways to improve the overall taste and/or odor of oral care raw materials such as those used in an oral care composition that are efficacious, cost-effective, and desirable to consumers.

SUMMARY OF THE INVENTION

It has now surprisingly been found that solvent extraction processes utilizing solvents such as ethyl acetate may be useful to significantly reduce the occurrence of non-polar materials found in oral care raw material compositions and thereby improve the oral care raw material's odor and/or taste profile.

Without being limited by theory, it is now believed that oral care raw materials previously generally thought to have bad taste and/or odor profiles stemming from the pure material itself may in fact have surprisingly more acceptable taste profiles. It has been surprisingly found that non-polar materials commonly present in commercially available oral care raw material compositions such as residual alcohols, alcohol ethoxylates, aldehydes, ethers, ketones, alkylamines, and esters, may be linked to a significant portion of the negative taste profiles previously associated with the raw materials themselves. Since some of these non-polar materials are often used in flavors and perfumes, it was further surprising that a new process for more efficiently extracting these materials from the underlying oral care raw material composition would produce such results. For example, dodecanol and dodecanal are commonly taught to be safe and useful for inclusion in flavors and perfumes, yet it has been surprisingly found that if included in oral care raw material compositions at significantly higher levels, these materials present an unpleasant taste such as bitter, soapy and the like.

Further without being limited by theory, solvent extraction using the appropriate solvent is more effective than previously known techniques to purify such oral care raw materials, allowing for the incorporation of such materials into oral care products with minimal negative taste and/or odor attributes.

The present invention is therefore directed to a process for improving the taste of oral care raw materials using solvent extraction, said process comprising the steps of: providing a solid oral care raw material composition in need of treatment wherein said oral care raw material composition comprises an orally acceptable raw material and one or more undesirable non-polar materials; contacting said oral care raw material composition with an extraction solvent to form an extraction mixture comprising a solid phase and a solvent phase; and separating the solid phase from the extraction mixture; wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

In one embodiment, the present invention relates to such processes wherein the extraction mixture further comprises from about 3% to about 90%, by weight of the composition, of water in an aqueous phase.

In another embodiment, the present invention relates to such processes wherein the oral care raw material is a solid material and is selected from metal salts, sweeteners, metal oxides, rheology modifiers, structurants, fillers, abrasives, inorganic phosphates, salt dyes, and mixtures thereof.

In another embodiment, the present invention relates to such processes wherein the oral care raw material is selected from zinc salts, sodium salts, potassium salts, calcium salts, magnesium salts, copper salts, zeolites, sodium saccharin, zinc oxide, titanium dioxide, cellulosic polymer rheology modifiers, polyethylene oxide, poloxamer, copolymers of acrylic acid crosslinked with a polyalkenyl polyether, maltodextrin, xanthan gum, and polyethylene glycols having a molecular weight of at least about 2000, calcium carbonate, silicas, pyrophosphates, sodium polyphosphates, cationic salt dyes, anionic salt dyes, and mixtures thereof.

In another embodiment, the present invention relates to such processes wherein the oral care raw material is a metal salt selected from sodium citrate, zinc citrate, stannous fluoride, stannous chloride, zinc lactate, calcium chloride, calcium carbonate, sodium hexametaphosphate, and mixtures thereof.

In another embodiment, the present invention relates to such processes wherein the oral care raw material is selected from stannous fluoride, sodium saccharin, copolymers of acrylic acid crosslinked with a polyalkenyl polyether, sodium acid pyrophosphate, zinc citrate, and mixtures thereof.

In another embodiment, the present invention relates to such processes wherein the oral care raw material is selected from stannous fluoride, sodium saccharin, copolymers of acrylic acid crosslinked with a polyalkenyl polyether, sodium acid pyrophosphate, and mixtures thereof.

In another embodiment, the present invention relates to such processes wherein the step of separating the solid phase from the extraction mixture comprises passing the extraction mixture through a filter and collecting the solid material.

In another embodiment, the present invention relates to such processes wherein the extraction solvent has individual Hansen solubility parameters of a dispersion force component ($\delta_D$) ranging from about 13 to about 19 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$ In another embodiment, the present invention relates to such processes wherein the extraction solvent is selected from ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters, supercritical carbon dioxide, and mixtures thereof.

In another embodiment, the present invention relates to such processes wherein the extraction solvent is selected from food grade ethyl esters.

In another embodiment, the present invention relates to such processes wherein the extraction solvent is ethyl acetate.

In another embodiment, the present invention relates to such processes wherein wherein the extraction mixture comprises from about 10% to about 90%, by weight of the mixture, of water; from about 5% to about 80%, by weight of the mixture, of oral care raw material; less than 10%, by weight of the oral care raw material, of undesirable non-polar impurities; and from about 10% to about 90%, by weight of the mixture, of solvent.

In another embodiment, the present invention relates to such processes wherein the ratio of extraction solvent to oral care raw material in the extraction mixture is from about 1:10 to about 10:1.

In another embodiment, the present invention relates to such processes wherein the step of separating the aqueous phase from the solvent phase further comprises centrifuging the extraction mixture.

In another embodiment, the present invention relates to such processes wherein the process further comprises mixing the extraction mixture for a period of from about 10 seconds to about one minute with vigorous mixing and at ambient temperature before allowing the mixture to settle into a least two phases and separating the aqueous phase from the solvent phase.

In another embodiment, the present invention relates to such processes wherein the process further comprises the step of removing any residual solvent from the aqueous phase wherein the step of removing any residual solvent from the aqueous phase includes the use of an industrial method selected from vacuum stripping (with or without heat), fractional distillation, wiped-film evaporator, carbon filtration, or combinations thereof.

In another embodiment, the present invention relates to such processes wherein the extraction mixture further comprises a phase separation enhancer selected from salt, pH modifiers, and mixtures thereof.

In another embodiment, the present invention relates to such processes wherein said process comprises the steps of: providing a solid oral care raw material composition in need of treatment wherein said oral care raw material composition comprises: i) an orally acceptable raw material selected from stannous fluoride, sodium saccharin, copolymers of acrylic acid crosslinked with a polyalkenyl polyether, sodium acid pyrophosphate, and mixtures thereof; and ii) one or more undesirable non-polar materials; contacting said oral care raw material composition with an extraction solvent to form an extraction mixture comprising a solid phase and a solvent phase; and separating the solid phase from the extraction mixture; wherein the extraction solvent is selected from food grade ethyl esters.

In another embodiment, the present invention relates to a treated oral care raw material composition comprising an oral care raw material and less than about 1%, by weight of the composition, of undesirable non-polar materials, produced by the processes herein.

In another embodiment, the present invention relates to such a treated oral care raw material composition wherein the treated oral care raw material composition comprises less than about 2%, by weight of the oral care raw material, of undesirable non-polar materials.

In another embodiment, the present invention relates to an oral care composition having improved consumer acceptance, wherein the oral care composition comprises an oral care raw material composition treated by the processes herein.

In another embodiment, the present invention relates to use of solvent extraction for improving the taste of oral care raw material compositions wherein ethyl acetate is used as an extraction solvent.

DETAILED DESCRIPTION OF THE INVENTION

The present invention relates to a process for improving the taste of oral care raw materials using solvent extraction, said process comprising the steps of:
a) providing a solid oral care raw material composition in need of treatment wherein said oral care raw material composition comprises an orally acceptable raw material and one or more undesirable non-polar materials;
b) contacting said oral care raw material composition with an extraction solvent to form an extraction mixture comprising a solid phase and a solvent phase; and
c) separating the solid phase from the extraction mixture;

wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

These elements will be discussed in more detail below.

Process for Improving the Taste of Oral Care Raw Materials

As used herein, solvent extraction, also known as partitioning, refers to a standard method to separate compounds based upon their relative solubilities, for instance, in two different immiscible liquids, such as water and a solvent. It is an extraction of a substance from one solid or liquid phase into another liquid phase.

In the extraction of materials from a solid, the undesirable non-polar materials are moved from the untreated oral care raw material into the solvent phase.

Optionally, the extraction also utilizes an aqueous phase such as where the solid oral care raw material is provided in a slurry. In one such embodiment, the "liquid-liquid" extraction phrase refers to the two different immiscible liquids that are mixed as part of the extraction procedure. As used herein, immiscible refers to the ability of the two liquids to form at least two layers when mixed together. The layers may be formed after mixing the two liquids and allowing them to sit at rest for a variable period of time, or in some instances, the mixture of the two liquids may be centrifuged and/or cooled below room temperature in order to assist the separation.

Typically in liquid-liquid extraction, one of the phases will be aqueous, and the other a non-polar lipophilic organic solvent such as ether, MTBE, dichloromethane, chloroform, or ethyl acetate. Most organic solvents float on top of an aqueous phase, though important exceptions are most halogenated solvents.

In one embodiment, an extraction contains a series of steps, providing fresh oral care raw material starting materials, production of the oral care raw material through traditional means, quenching the reaction, optional intermediate processing and/or cleanup and providing the oral care raw material composition in need of treatment, contacting the oral care raw material composition with an extraction solvent, and optionally water to form an extraction mixture containing solid phase and solvent phase, optionally an aqueous phase, separating the liquid phases with optional centrifuge and optional repeating of the extraction steps, separating residual volatile solvent from the aqueous phase or solid phase by means such as vacuum stripping, heating, wiped-film evaporation or combinations thereof, collecting the improved oral care raw material, conducting fractional distillation on the organic phase to recover the extraction solvent for future use, collect the undesirable non-polar materials and separate into valuable and unusable non-polar materials (impurities) including the step of recovering the starting oral care raw material.

In one embodiment, an extraction process will use an extraction step in which undesirable non-polar materials are transferred from the aqueous phase to the solvent phase and then optionally followed by a scrubbing stage in which the undesirable non-polar materials are removed from the solvent phase, then optionally followed by a stripping stage in which any oral care raw materials or other materials are removed from the solvent phase. The solvent phase may then be treated to make it ready for use again.

In one embodiment, the process includes a step of collecting the oral care raw material from the extraction mixture, and optionally from the aqueous phase. In another embodiment, after the step of collecting the oral care raw material from the extraction mixture and/or aqueous phase, the oral care raw material is subjected to one or more of the following:

a) at least one repeat of the process steps, optionally repeating the steps of the process at least 3 times, optionally repeating the steps of the process at least 4 times, in succession;

b) a further filtration step, optionally using carbon filtration; and/or c) incorporation of the oral care raw material into an oral care composition.

Providing a Oral Care Raw Material Composition in Need of Treatment

Oral Care Raw Material

As used herein "oral care raw material" refers to any solid raw materials suitable for use (considering safety) in oral care compositions. Oral care raw material compositions include an oral care raw material and the undesirable non-polar materials commonly found in commercially available materials.

Oral care raw materials useful in the processes herein include metal salts, sweeteners, metal oxides, rheology modifiers, structurants, fillers, abrasives, inorganic phosphates, salt dyes, and mixtures thereof.

Metal salts useful herein include stannous salts, zinc salts (for example, zinc citrate and zinc lactate), sodium salts (for example, sodium citrate and sodium fluoride), potassium salts (for example potassium nitrate), calcium salts, magnesium salts, copper salts, zeolites, and mixtures thereof. Metal salts have a wide range of functions from antimicrobial agents to sensitivity agents and/or buffers.

In a further embodiment, the zinc salt is selected from zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, zinc oxide, and combinations thereof. In an additional embodiment, the potassium salt is selected from the group consisting of potassium nitrate, potassium citrate, potassium oxalate, potassium bicarbonate, potassium acetate, potassium chloride, and combinations thereof. In an additional embodiment, the copper salt is selected from the group consisting of copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In another embodiment, the stannous salt is selected from the group consisting of stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, stannous gluconate, and combinations thereof.

Sweeteners useful herein include sodium saccharin. Metal oxides useful herein include zinc oxide and titanium dioxide.

Rheology modifiers useful herein include cellulosic polymers (for example, carboxymethylcelluloses, hydroxyethylcelluloses), polyethylene oxide, poloxamer, CARBOPOL type copolymers of acrylic acid crosslinked with a polyalkenyl polyether, maltodextrin, xanthan gum, polyethylene glycols having a molecular weight of 2000 and higher, and mixtures thereof.

Filler/Abrasives—Calcium Carbonate, Silicas, Zeolites

Inorganic phosphates useful herein include pyrophosphates, sodium polyphosphates (for example, sodium hexametaphosphate, and mixtures thereof.

Salt dyes useful herein include solid cationic, anionic or mixtures thereof. For example, FD&C No. 1.

Oral care raw materials may be treated by the processes herein individually or in a mixture of oral care raw materials.

In one embodiment, the oral care raw material is selected from zinc salts, sodium salts, potassium salts, calcium salts, magnesium salts, copper salts, zeolites, sodium saccharin, zinc oxide, titanium dioxide, cellulosic polymer rheology modifiers, polyethylene oxide, poloxamer, copolymers of acrylic acid crosslinked with a polyalkenyl polyether, maltodextrin, xanthan gum, and polyethylene glycols having a molecular weight of at least about 2000, calcium carbonate, silicas, pyrophosphates, sodium polyphosphates, cationic salt dyes, anionic salt dyes, and mixtures thereof.

In another embodiment, the oral care raw material is a metal salt selected from sodium citrate, zinc citrate, stannous fluoride, stannous chloride, zinc lactate, calcium chloride, calcium carbonate, sodium hexametaphosphate, and mixtures thereof.

In another embodiment, the oral care raw material is selected from stannous fluoride, sodium saccharin, copolymers of acrylic acid crosslinked with a polyalkenyl polyether, sodium acid pyrophosphate, zinc citrate, and mixtures thereof. In another embodiment, the oral care raw material is selected from stannous fluoride, sodium saccharin, copolymers of acrylic acid crosslinked with a polyalkenyl polyether, sodium acid pyrophosphate, and mixtures thereof.

Undesirable Non-polar Materials

As used herein "undesirable non-polar materials" refers generally to any non-polar materials that are found in the oral care raw material composition in need of treatment. In one embodiment, the undesirable non-polar materials are selected from residual alcohols, alcohol ethoxylates, aldehydes, ethers, ketones, alkylamines, amides, and esters.

In one embodiment, the undesirable non-polar materials may be off-tasting components selected from impurities, unreacted starting materials, by-products and/or contaminants. Such undesirable non-polar materials may be described by consumers as soapy, bitter, metallic, earthy or dirty, and astringent. Soapy is typically characterized by the presence of dodecanal or dodecanol. Bitter taste may occur in the presence of alkyl amines or alcohols.

Extraction Mixture

In one step of the process herein, the oral care raw material composition is contacted with an extraction solvent and optionally water to form an extraction mixture comprising a solid phase, a solvent phase and optionally an aqueous phase. In one embodiment, such as in a laboratory-scale batch process, the extraction mixture is then mixed vigorously for a period of from about 10 seconds to one minute or more. After mixing, the extraction mixture is allowed to rest for a period of from about 15 minutes to about 2 hours. Where multiple extractions are conducted in succession, the separation time may be shortened to a period of from about 10 to about 20 minutes.

In another embodiment, such as on an industrial scale, an industrial centrifuge extractor such as the BXP 190 manufactured by Rousselet Robatel may be used to take advantage of the density differences between the solid and solvent phases or two fluids to separate them via centrifugation. The devices can be operated in a countercurrent setup or as single stage extractions. Successive continuous extractions using an industrial centrifuge extractor can occur quite quickly, even in a matter of seconds, to reach the desired treated oral care raw material.

The extraction mixture then contains the extraction solvent, oral care raw material and undesirable non-polar materials. In one embodiment, the extraction mixture comprises from about 10% to about 90%, by weight of the mixture, of water; from about 5% to about 60%, by weight of the mixture, of oral care raw material; less than 5%, by weight of the mixture, of undesirable non-polar materials; and from about 10% to about 90%, by weight of the mixture, of solvent. In one embodiment, the ratio of extraction solvent to oral care raw material in the extraction mixture is from about 1:10 to about 10:1, alternatively is from about 1:2 to about 2:1.

The water included in the extraction mixture may be provided in the oral care raw material composition itself when obtained as an aqueous solution from the commercial supplier and/or may be water that is added during the extraction process. In some instances, the water level in a oral care raw material aqueous solution may be reduced before contacting the oral care raw material composition with the extraction solvent to reduce the level of solvent needed for the processes herein.

In one embodiment, the extraction mixture further comprises a phase separation enhancer selected from salts, pH modifiers, and mixtures thereof.

In one embodiment, after the extraction mixture is formed and contains both an aqueous phase and a solvent phase, the aqueous phase is then separated from the solvent phase. In another embodiment, after the two phases are separated, the extraction solvent is recovered from the solvent phase and reused in subsequent liquid-liquid extraction processes.

In one embodiment, during the step of separating the aqueous phase from the solvent, the temperature is adjusted to improve the extraction efficiency. As used herein, "extraction efficiency" refers to the ability of the process to remove undesirable impurities from the oral care raw material composition in need of treatment.

In one embodiment, during the process, the pressure under which the process takes place is adjusted to improve the extraction efficiency.

In one embodiment, the process steps herein are repeated in succession until the desired amount of undesirable non-polar impurities is removed. In one embodiment, the treated oral care raw material composition is collected and the process steps are repeated at least two times, alternatively at least 3 times, still alternatively at least 4 times in succession, each time further reducing the level of undesirable water-soluble impurities.

In another embodiment, multiple extractions are performed in series after removal of the extraction solvent from preceding extraction.

As used herein, the terms "extract" and "extraction" refer to the process of removing undesirable components from the desirable components of the oral care raw material composition. The undesirable components could be associated with microorganism removal and/or other impurity or contaminant removal, primarily via preferential solubility in the extraction solvent.

As used herein, the terms "removal", "reduce", "reduction", and their derivatives refer to partial reduction of the number or concentration of undesirable materials and may be considered in a relative sense, particularly when multiple repetitions of the process steps herein are used in succession on the same starting material.

Extraction Solvent

As used herein, "extraction solvent" refers to any liquid or supercritical fluid that can be used to solubilize undesirable non-polar materials that are contained within an oral care raw material composition. Organic solvents with acceptable safety profiles that will form a liquid bilayer with an aqueous phase could be used either alone or in combination with other solvents such as ethyl acetate, ethanol, propylene glycol, PEGs, other ethers or esters, or other solvents, etc. to achieve a similar result. One example of a useful supercritical fluid is carbon dioxide. A range of ratios of solvent to oral care raw material, a range of oral care raw material concentrations, the mixing and/or extraction conditions, etc. are variables that could be optimized for a particular application of this general approach.

Without being limited by theory, when thorough chemical composition data on the undesirable non-polar materials found in the oral care raw material composition in need of treatment are obtained through in-depth chemical characterization and are well-understood, an investigation can be initiated to determine if the impurities are primarily responsible for malodors and off-tastes, or if the oral care raw materials themselves are contributing a large fraction of the malodors and off tastes.

Extraction solvents useful herein include those having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

In one embodiment, the solvent has individual Hansen solubility parameters of a dispersion force component ($\delta_D$) ranging from about 13 to about 19 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$. In one embodiment, the polar component ranges from about 4 to about 6, in another embodiment, the hydrogen bonding component ranges from about 6 to about 9.

In one embodiment, the extraction solvents useful herein have a logP value of greater than 0.5.

Extraction solvents useful herein include ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters and mixtures thereof. In one embodiment, the extraction solvent is selected from food grade ethyl esters.

Other extraction solvents useful herein include ketones such as methyl ethyl ketone, ethers such as di-n-propyl ether, lactones, acetals, and mixtures thereof.

Other extraction solvents useful herein include those selected from hexane, cyclohexane, heptane, chloroform, toluene, methylene chloride, methyl nonafluoroether, ethyl nonafluoroether, carbon tetrachloride, and mixtures thereof. HFE 7100, HFE 7200, and HFE 7500 are tradenames of commercially available hydrofluoroethers available from TCI AMERICA, 9211 N. Harborgate Street, Portland, Oreg. 97203, U.S.A.

Mixtures of extraction solvents may also be used.

In one embodiment, the extraction mixture is substantially free of (i.e. comprises no reasonably measurable quantity of) 1-octanol and phenoxy ethanol.

Extraction solvents useful herein also include supercritical fluids such as carbon dioxide. As used herein, "supercritical carbon dioxide" is carbon dioxide that is at a temperature and a pressure greater than Tr=1 and Pr=1. Tr is T/Tc where T is the present temperature of the supercritical carbon dioxide and Tc is the critical temperature. Pr is P/Pc where P is the present pressure of the supercritical carbon dioxide and Pc is the critical pressure. Tc, the critical temperature for carbon dioxide ($CO\_$), is 31.1 degrees Celsius (deg. C.), or 304.1 degrees Kelvin (K), and Pc is 73 atmospheres (atm) or about 1073 pounds per square inch (PSI).

In more general terms, supercritical carbon dioxide refers to carbon dioxide that is in a fluid state while also being at or above both its critical temperature and pressure. Carbon dioxide usually behaves as a gas in air at standard temperature and pressure (STP) or as a solid called dry ice when frozen. If the temperature and pressure are both increased from standard temperature and pressure to be at or above the critical point for carbon dioxide, it can adopt properties midway between a gas and a liquid. More specifically, it behaves as a supercritical fluid above its critical temperature (31.1 deg. C.) and critical pressure (73 atm), expanding to fill its container like a gas but with a density like that of a liquid. The supercritical fluid region of the phase diagram is defined as a temperature above the critical temperature (31.1 deg. C.) to a pressure above the critical pressure (73.8 bar or 1070 PSI).

When using a supercritical fluid as the extraction solvent, it is possible to choose a "batch-type" system or choose a "continuous-type" system. The batch systems can be used in parallel or in series, operated on a cyclic basis (at prescribed residence times), be sequentially loaded, processed, and unloaded, and yield a sufficient hulk removal efficiency. The "continuous-type" systems generally refer to a number of batch vessels, operated sequentially, with the supercritical carbon dioxide gas flow and the sequential loading, processing, and unloading of the feed and product solids can be envisioned as counter current flow of the solids movement from feed to product with respect to the flow of the supercritical carbon dioxide. The directional loading, processing, and unloading is opposite to the flow of the supercritical carbon dioxide. This type of "continuous", counter current operation is generally referred to as continuous, counter current, sequencing-batch operation. Therefore, when there are one or two batch stages, in series or parallel, the term "batch" tends to be used, and when there are three or more stages, if they operate in parallel flow to the supercritical carbon dioxide, the term "batch" is also used. However, when they operate in counter current flow of the material to be extracted to the supercritical carbon dioxide, we call them counter current "sequencing-batch" simulating counter current flows of material feed and desired product to the flow direction of the supercritical carbon dioxide. It should be understood that "continuous" can also define a process in which the feed and solvent are fed continuously through a fixed system and the products are continuously removed.

When the supercritical fluid is selected as the extraction solvent, the separation of the aqueous phase from the solvent phase may occur by releasing the temperature and pressure placed upon the supercritical fluid, allowing the fluid to return to a gaseous state.

Selection of an Extraction Solvent

In one embodiment, the process further comprises a step of selecting an extraction solvent suitable for use with the oral care raw material in need of treatment.

Such step includes evaluating the extraction solvent under consideration with the oral care raw material in need of treatment. Evaluation of the solvent includes combining the proposed solvent with the oral care raw material composition in need of treatment to determine whether the solvent forms a 2-phase system with the oral care raw material water mixture. The pH, temperature, or ionic strength may be adjusted to deliver a good two-phase break, and also to optimize the extraction efficiency. The extraction solvent should not cause significant precipitation when combined with the water/oral care raw material mixture. Since a successful two-phase separation will be achieved with suitable extraction solvents, the solvent polarity is expected to preferentially extract non-polar impurities into the extraction solvent layer and away from the aqueous oral care raw material phase. In one embodiment, the solvent will be food grade and easily separable from the aqueous/oral care raw material phase. Selection of a solvent that is easily recoverable from the extracted impurities is also desirable, i.e. by fractional distillation, so that it can be re-used for subsequent extractions. The solvents selected for the solubilization method of this invention are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," Edited by Allan F. M. Barton (1999). Each material is defined by three points in 3D space and these three points are known as the Hansen Solubility Parameters (HSP) which may be defined as follows.

Solubility parameters are theoretically calculated numerical constants which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically- and theoretically-derived solubility parameters, a dispersion-force component ($\delta_D$), a polar or dipole interaction component ($\delta_P$) and a hydrogen-bonding component ($\delta_H$). Each of the three parameters (i.e., dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$ or $(J/cc)^{0.5}$.

These three parameters can be treated as co-ordinates for a point in three dimensions also known as the Hansen space. The nearer two molecules are in this three dimensional space, the more likely they are to dissolve into each other. To determine if the parameters of two molecules (usually a solvent and a polymer) are within range a value called interaction radius ($R_O$) is given to the substance being dissolved. This value determines the radius of the sphere in Hansen space and its center is the three Hansen parameters. To calculate the distance (Ra) between Hansen parameters in Hansen space the following formula is used.

$$(Ra)^2 = 4(\delta_{d2}-\delta_{d1})^2 + (\delta_{p2}-\delta_{p1})^2 + (\delta_{b2}-\delta_{h1})^2$$

The Hansen solubility parameters can be calculated by "Molecular Modeling Pro" software, version 5.1.9 (ChemSW, Fairfield Calif., www.chemsw.com) or Hansen Solubility from Dynacomp Software. The solubility parameters of solvents useful herein are shown in Table 1, below.

TABLE 1

| Component | Dispersion ($\delta D$) | Polarity ($\delta P$) | Hydrogen Bonding ($\delta H$) | Ra (With Ethyl Acetate) | Ra (With Dodecanol) |
|---|---|---|---|---|---|
| ethyl acetate | 15.8 | 5.3 | 7.2 | 0 | 4.5 |
| carbon dioxide | 15.7 | 6.3 | 5.7 | 1.8 | 5.7 |
| hexane | 14.9 | 0 | 0 | 9.1 | 10.0 |
| heptanes | 15.3 | 0 | 0 | 9 | 10.2 |
| benzene | 18.4 | 0 | 2 | 9.1 | 11.8 |
| diethyl ether | 14.5 | 2.9 | 5.1 | 4.1 | 4.3 |
| di-n-propyl ether | 15.5 | 2.3 | 4.5 | 4.1 | 5.7 |
| methylene chloride | 18.2 | 6.3 | 6.1 | 5 | 9.4 |
| carbon tetrachloride | 17.8 | 0 | 0.6 | 9.4 | 12.0 |
| propylene carbonate | 20 | 18 | 4.1 | 15.5 | 19.6 |
| propylene glycol methyl ether acetate | 15.6 | 5.6 | 9.8 | 2.6 | 3.9 |
| 1,1,1-trichloroethane | 16.8 | 4.3 | 2 | 5.7 | 9.2 |
| methyl nonafluorobutyl ether* | 13.74 | 3.59 | 4.14 | 5.4 | 5.2 |
| ethyl nonafluorobutyl ether* | 14.31 | 4.36 | 3.98 | 4.5 | 5.5 |

*Methyl and Ethyl Nonafluorobutyl Ethers are commercially available from TCI AMERICA, 9211 N. Harborgate Street, Portland, OR 97203, U.S.A.

Solid Phase

As used herein, "solid phase" refers to the portion of the extraction mixture containing an oral care raw material that remains a solid during the extraction process.

In one embodiment, undesirable non-polar impurities are directly extracted into the extraction solvent from the solid phase.

In another embodiment, water is added to the solid phase consisting of oral care raw materials to create a slurry prior to extraction with an extraction solvent to remove undesirable non-polar impurities.

Aqueous Phase

As used herein, "aqueous phase" refers to the portion of the extraction mixture containing water, oral care raw material, and other water-soluble materials.

In one embodiment, the processes of the present invention may further include a step of adjusting the ionic strength or pH of the aqueous phase up or down to improve the extraction efficiency.

In another embodiment, a solid raw material may be dissolved in an aqueous phase prior to extracting undesirable non-polar impurities with an extraction solvent.

In another embodiment, water may be added to a solid raw material, where the solid raw material is not soluble in water, to create an aqueous slurry prior to removal of the undesirable non-polar impurities with an extraction solvent.

Solvent Phase

As used herein, "solvent phase" refers to the portion of the extraction mixture containing the extraction solvent, the undesirable non-polar materials, and other water-insoluble materials.

Generally, the solvent phase and the aqueous phase will be immiscible.

In one embodiment, after separation of the aqueous and solvent phases, the aqueous phase still contains small amounts of the extraction solvent and the extraction solvent may be further removed from the aqueous phase by subsequent extraction steps, evaporation (such as with a rotavapor or open-air, optionally with a nitrogen stream) or combinations thereof.

Separating the Aqueous Phase from the Solvent Phase

As discussed more fully above, the separation of the aqueous phase from the solvent phase may occur using traditional liquid-liquid extraction techniques. Such separation may be crudely done based upon the phase break, particularly where multiple rounds of extraction are planned. On a lab bench or pilot plant scale this may mean by use of a separatory funnel, while on an industrial scale, this may mean by use of standard equipment for centrifugation and separation in a continuous process or in very large tanks equipped for separation on a batch basis.

In one embodiment, the step of separating the aqueous phase from the solvent phase further comprises centrifuging the extraction mixture.

In one embodiment, the extraction mixture is mixed for from about 10 seconds to about one minute with vigorous mixing and at ambient temperature before allowing the mixture to settle into two phases and separating the aqueous phase from the solvent phase.

In one embodiment, the step of separating the aqueous phase from the solvent phase comprises reducing the heat and pressure applied to a supercritical fluid, such as carbon dioxide, allowing the supercritical fluid to return to a gaseous state, and allowing the gas to escape from the extraction mixture.

The process may further comprise the step of removing any residual solvent from the aqueous phase. In one embodiment the step of removing any residual solvent from the aqueous phase includes the use of an industrial method selected from vacuum stripping (with or without heat), fractional distillation, wiped-film evaporation, carbon filtration, or combinations thereof.

Recovering the Treated Oral Care Raw Material

The processes according to the present invention may further include a step of recovering the treated oral care raw material composition from the aqueous phase by evaporation or other traditional means.

In one embodiment, the treated oral care raw material composition contains from about 10% to about 50%, alternatively from about 20% to about 30% of the treated oral care raw material, from about 60 to about 90%, alternatively from about 70% to about 80% water, and 1% or less, alternatively 0.7% or less, alternatively 0.5% or less, alternatively 0.1% or less, alternatively 0.05% or less, alternatively 0.01% or less, of undesirable non-polar materials, all by weight of the treated composition.

In one embodiment, the treated oral care raw material composition contains from about 99% to about 100%, treated oral care raw material and 1% or less, alternatively 0.7% or less, alternatively 0.5% or less, alternatively 0.1% or less, alternatively 0.05% or less, alternatively 0.01% or less, of undesirable non-polar materials, all by weight of the treated composition.

In one embodiment, the treated oral care raw material composition contains 0.7% or less, alternatively 0.5% or less, alternatively 0.1% or less, alternatively 0.05% or less, alternatively 0.01% or less, by weight of the treated composition, of undesirable non-polar materials.

In one embodiment, the treated oral care raw material composition contains from about 10% to about 50%, alternatively from about 20% to about 30% of the treated oral care raw material, from about 60 to about 90%, alternatively from about 70% to about 80% water, and 1% or less of total alcohols, all by weight of the treated composition.

Recycling the Solvent

In one embodiment, the process further includes a step of separating the extraction solvent from the solvent phase and optionally reusing the extraction solvent for further liquid-liquid extraction processes.

In one embodiment, the step of recycling the solvent includes the use of a fractionating column (or distillation tower). Fractionating columns have been shown capable of separating these types of streams and removing them for varying uses. Design of the fractionating column will need to take into account the potential markets for the varying fractions, throughput needs for the system, and overall costs. The size and number of plates used in the distillation tower may be selected with these factors in mind A fractionating column or fractionation column may be used in the distillation of liquid mixtures so as to separate the mixture into its component parts, or fractions, based on the differences in their volatilities. Fractionating columns may vary in size and are used in small scale laboratory distillations as well as for large-scale industrial distillations.

Fractionating columns help to separate the mixture by allowing the mixed vapors to cool, condense, and vaporize again in accordance with Raoult's law. With each condensation-vaporization cycle, the vapors are enriched in a certain component.

In a typical fractional distillation, a liquid mixture is heated in the distilling flask, and the resulting vapor rises up the fractionating column. The vapor condenses on glass spurs (known as trays or plates) inside the column, and returns to the distilling flask, refluxing the rising distillate vapor. The hottest tray is at the bottom of the column and the coolest tray is at the top. At steady-state conditions, the vapor and liquid on each tray reach an equilibrium. Only the most volatile of the vapors stays in gas form all the way to the top, where it may then proceed through a condenser, which cools the vapor until it condenses into a liquid distillate. The separation may be enhanced by the addition of more trays (to a practical limitation of heat, flow, etc.).

Fractional distillation is one of the unit operations of chemical engineering. Fractionating columns are widely used in the chemical process industries where large quantities of liquids have to be distilled. Many fractions can be recovered through this method and for industrial processes, the limitation is typically only product requirements and economics.

Industrial distillation is typically performed in large, vertical cylindrical columns known as "distillation towers" or "distillation columns" with diameters ranging from about 65 centimeters to 6 meters and heights ranging from about 6 meters to 60 meters or more. Industrial distillation towers are usually operated at a continuous steady state. Unless disturbed by changes in feed, heat, ambient temperature, or condensing, the amount of feed being added normally equals the amount of product being removed.

Other means of recycling the solvent phase include use of a cyclone separator. It may be possible to use the density differences of the materials in the solvent phase to drive their separation. This approach has the advantage of typically being more economical to install and operate, but may reduce the degree of separation that can be achieved versus a distillation approach.

Incorporating into Oral Care Compositions

The processes of the present invention may further include a step of incorporating the treated oral care raw material composition into an oral care composition.

Oral Care Compositions

The treated oral care raw material compositions resulting from the processes according to the present invention, may, in one embodiment, be incorporated into an oral care composition having improved taste vs. a oral care raw material untreated by the processes set forth herein.

As used herein, "oral care composition" is meant a product, which in the ordinary course of usage, is not intentionally swallowed for purposes of systemic administration of particular therapeutic agents, but rather is retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

EXAMPLES

Example I

Improved Sodium Acid Pyrophosphate

Undesirable non-polar materials were extracted from sodium acid pyrophosphate solid raw material, supplied by Prayon, Incorporated (Augusta, Ga., USA), using the following process steps:
1. Weigh ~5.0 grams of solid raw material and transfer into a clean 50 mL Falcon polypropylene centrifuge tube.
2. Add 50 mL of ethyl acetate (EtOAc, supplied by Sigma Aldrich, St. Louis, Mo., USA), using a graduated cylinder.
3. Cap the centrifuge tube and hand mix by gentle shaking for 5 minutes.
4. Vortex the capped centrifuge tube at 2500 rpm for 5 minutes using a VWR Signature Mini Digital Vortex Mixer (Henry Troemner, Thorofare, N.J., USA).
5. Allow 3-5 minutes for the solid material to settle to the bottom of the tube.
6. Decant the liquid and collect separately.
7. Measure a fresh 50 mL aliquot of EtOAc and add it to the solid material. Follow steps 2-6 two more times, for a total of three EtOAc extractions.
8. After decanting the liquid EtOAC following the third extraction, place the centrifuge tube horizontal in a fume hood uncapped, and allow the residual ethyl acetate to evaporate.

To determine the effectiveness of this procedure for removing undesirable, non-polar impurities, the pre- and post-extracted sodium acid pyrophosphate raw materials were prepared in aqueous solution (about 4:1 water:raw material ratio) and analyzed by immersion solid phase micro-extraction (SPME) GC-FID (using an Agilent Model 7890 gas chromatograph (GC), Agilent Technologies, Wilmington, Del., USA equipped with a flame ionization detector (FID)). The percent reduction of the undesirable materials from the commercially supplied material is set forth in Table 2, below.

TABLE 2

GC-FID analysis of sodium acid pyrophosphate raw material before and after LLE treatment with EtOAc.

| Sodium Acid Pyrophosphate | Total Volatile Peak Area (GC/FID) | |
|---|---|---|
| | $1^{st}$ Measurement | $2^{nd}$ Measurement |
| Control (Pre-extract) | 6,445,383 | 6,177,331 |
| Post-extract | 230,041 | 225,938 |
| % Reduction | 96.4 | |

Treated raw materials were evaluated relative to the untreated (control) raw materials for sensory impact on dentifrice brushing experience. Two batches of dentifrice were prepared according to the formulation set forth in Table 3 below. One dentifrice batch was prepared with treated sodium acid pyrophosphate and treated cocamidylpropyl betaine (Evonik Goldschmidt Corporation, Hopewell, Va., USA) while the other dentifrice batch was prepared from control or untreated raw materials. The other raw materials in the dentifrice formulation were not treated in this example. The suppliers and grades of all raw materials utilized in this example are typically and commonly used for production of oral care dentifrice formulations.

TABLE 3

Dentifrice formulation utilized for sensory evaluation of treated and untreated dentifrice raw materials.

| Raw Material | Percentage in Dentifrice |
|---|---|
| Water | 4.34 |
| Sorbitol | 29.43 |
| Sodium Acid Pyrophosphate | 2.00 |
| Titanium Dioxide | 0.53 |
| Carboxy Methyl Cellulose | 0.80 |
| Tri Sodium Phosphate | 1.10 |
| Water | 6.64 |
| Cocamidopropyl Betaine | 8.00 |
| Sorbitol | 20.20 |
| Silica 119 | 15.00 |
| Sodium Phosphate Monobasic | 0.42 |
| Carbomer | 0.30 |
| Sodium Saccharin | 0.30 |
| Sodium Lauryl Sulfate | 4.00 |
| Sorbitol | 6.14 |
| Peppermint Flavor | 0.80 |
| Total = | 100.00 |

Dentifrice test products were prepared with treated and untreated raw materials and then subjected to comparative taste testing by sensory experts. Panelists were instructed not to eat or drink within 30 minutes before brushing. They were also instructed to allow at least 2 hours from the last time they had brushed in order to provide enough time for the palate to clear between brushings. Panelists were specifically instructed to:

1) Dispense test product onto their toothbrush, as they normally would.
2) Before brushing, take pea size amount of dentifrice onto their tongue and swish it around their mouths for ~15 seconds.
3) Brush their teeth as they normally would.
4) Expectorate, rinse with water and then fill out a questionnaire asking for a numerical rating of (A) bitterness, (B) cool & refreshing aftertaste, (C) undesirable aftertaste, and (D) overall liking on a scale from 0 to 60.

The panelists were provided test dentifrice products in white tubes with only numerical labels, so as not to reveal detailed information about the contents of each tube. The numerical label along with the details of each tube's contents are provided below:

264=Dentifrice prepared with untreated sodium acid pyrophosphate and untreated cocamidopropyl betaine (control). All other raw materials were also untreated.

578=Dentifrice prepared with treated sodium acid pyrophosphate and treated cocamidopropyl betaine. All other raw materials were untreated.

Table 4 summarizes the panelist ratings of key attributes during their brushing experience with these dentifrice test products. As shown, dentifrice prepared with treated raw materials clearly reduces bitterness and undesirable aftertaste, while also improving the cool and refreshing after taste, as well as overall liking of the dentifrice.

TABLE 4

Panelist ratings of dentifrice prepared with untreated (control) and treated raw materials.

| Attribute (n = 4) | 264 Control (Untreated) | 578 Treated |
|---|---|---|
| Bitterness | 44.00 | 28.00 |
| Cool & Refreshing Aftertaste | 31.25 | 40.50 |
| Undesirable Aftertaste | 29.50 | 15.00 |
| Overall Liking | 33.25 | 39.00 |

Example II

Improved Sodium Fluoride

Undesirable non-polar materials were extracted from sodium fluoride solid raw material, supplied by Sigma-Aldrich, Company (St. Louis, Mo., USA), using the process steps shown in Example I, substituting sodium fluoride as the solid raw material. This source and grade of sodium fluoride is relatively lower quality than GMP sources of sodium fluoride with supplier stated purity of this material at 99%. This lower grade of material is useful in this example to demonstrate that a relatively lower quality of material can be treated with this procedure to substantially reduce the volatile impurities. As in Example I, to determine the effectiveness of this procedure at removing undesirable, non-polar impurities the pre- and post-extraction sodium fluoride raw materials were analyzed by immersion SPME GC-FID. The percent reduction of the undesirable materials from the commercially supplied material is set forth in Table 5, below.

TABLE 5

GC-FID analysis of sodium fluoride raw material before and after LLE treatment with EtOAc.

| Sodium Fluoride | Total Volatile Peak Area (GC/FID) | |
|---|---|---|
|  | $1^{st}$ Measurement | $2^{nd}$ Measurement |
| Control (Pre-extract) | 3,781,285 | 4,022,665 |
| Post-extract | 151,811 | 209,947 |
| % Reduction | 95.4 | |

Example III

Improved Zeodent 119 Silica

Undesirable non-polar materials were extracted from zeodent 119 silica solid raw material, supplied by JM Huber Corp (Etowah, Tenn., USA), using the process steps shown in Example I, substituting zeodent 119 silica as the solid raw material. As in Example I, to determine the effectiveness of this procedure at removing undesirable, non-polar impurities the pre- and post-extraction zeodent 119 silica raw materials were analyzed by immersion SPME GC-FID. The percent reduction of the undesirable materials from the commercially supplied material is set forth in Table 6, below.

TABLE 6

GC-FID analysis of zeodent 119 silica raw material before and after LLE treatment with EtOAc.

| Zeodent 119 Silica | Total Volatile Peak Area (GC/FID) | |
|---|---|---|
|  | $1^{st}$ Measurement | $2^{nd}$ Measurement |
| Control (Pre-extract) | 37,221,176 | 33,075,713 |
| Post-extract | 10,582,986 | 9,750,069 |
| % Reduction | 71.1 | |

Example IV

Improved Zinc Lactate

Undesirable non-polar materials were extracted from zinc lactate solid raw material, supplied by Purac America Company, Inc. (Blair, Nebr., USA), using the process steps shown in Example I, substituting zinc lactate as the solid raw material. To determine the effectiveness of this procedure at removing undesirable, non-polar impurities, the pre- and post-extraction zinc lactate raw materials were analyzed, in this case, by headspace sampling over a dry aliquot of solid material followed by SPME GC-FID. The percent reduction of the undesirable materials from the commercially supplied material is set forth in Table 7, below.

TABLE 7

GC-FID analysis of zinc lactate raw material before and after LLE treatment with EtOAc.

| Zinc Lactate | Total Volatile Peak Area (GC/FID) | |
|---|---|---|
|  | $1^{st}$ Measurement | $2^{nd}$ Measurement |
| Control (Pre-extract) | 1,782,352 | 1,712,978 |
| Post-extract | 525,911 | 478,163 |
| % Reduction | 71.3 | |

Example V

Improved Carbopol (Carbomer 956)

Undesirable non-polar materials were extracted from carbopol solid raw material, supplied by The Lubrizol Corporation (Louisville, Ky., USA), using the process steps shown in Example I, substituting carbopol as the solid raw material. To determine the effectiveness of this procedure at removing undesirable, non-polar impurities, in this case, the pre- and post-extraction cabopol raw materials were analyzed by headspace sampling over a dry aliquot of solid material by SPME GC-FID. The percent reduction of the undesirable materials from the commercially supplied material is set forth in Table 8, below.

TABLE 8

GC-FID analysis of carbopol raw material before and after LLE treatment with EtOAc.

| Carbopol | Total Volatile Peak Area (GC/FID) | |
|---|---|---|
| | 1$^{st}$ Measurement | 2$^{nd}$ Measurement |
| Control (Pre-extract) | 213,950,556 | 164,213,445 |
| Post-extract | 71,648,122 | 60,062,749 |
| % Reduction | 65.2 | |

Example VI

Improved Zeodent 109 Silica

Undesirable non-polar materials were extracted from zeodent 109 silica solid raw material, supplied by JM Huber Corp (Etowah, Tenn., USA), using the process steps shown in Example I, substituting zeodent 109 silica as the solid raw material. As in Example I, to determine the effectiveness of this procedure at removing undesirable, non-polar impurities the pre- and post-extraction zeodent 109 silica raw materials were analyzed by immersion SPME GC-FID. The percent reduction of the undesirable materials from the commercially supplied material is set forth in Table 9, below.

TABLE 9

GC-FID analysis of zeodent 109 silica raw material before and after LLE treatment with EtOAc.

| Zeodent 109 Silica | Total Volatile Peak Area (GC/FID) | |
|---|---|---|
| | 1$^{st}$ Measurement | 2$^{nd}$ Measurement |
| Control (Pre-extract) | 9,235,217 | 11,179,621 |
| Post-extract | 3,824,626 | 3,718,197 |
| % Reduction | 63.1 | |

Example VII

Improved Zinc Citrate

Undesirable non-polar materials were extracted from zinc citrate solid raw material, supplied by Jost Chemical Company (St. Louis, Mo., USA), except in this case, an aqueous slurry with deionized water was created during the extraction procedure, as described in the process steps below:

1. Weigh ~2.0 grams of solid raw material and transfer into a clean 50 mL Falcon polypropylene centrifuge tube.
2. Add 8 mL of deionized water, using a graduated cylinder, and shake the mixture well manually.
3. Add 12 mL of ethyl acetate (supplied by Sigma Aldrich, St. Louis, Mo., USA) with a graduated cylinder.
4. Cap the centrifuge tube and vortex for 1 minute using an S/P® Vortex Mixer (Baxter Diagnostics Inc., Deerfield, Ill., USA) at high speed.
5. Centrifuge the mixture at 2500 rpm/25° C. for 5 minutes (IEC Centra GP8R, International Equipment Company; Needham HTS., MA, USA).
6. Remove the upper ethyl acetate supernatant layer with a glass pipette.
7. Measure a fresh 12-mL aliquot of EtOAc and add it to the remaining mixture containing zinc citrate, water, and residual ethyl acetate. Follow steps 3-6 two more times, for a total of three EtOAc extractions.
8. Following the third extraction, decant all liquid supernatant (both ethyl acetate and water) after centrifugation and place the centrifuge tube horizontal in a fume hood uncapped, and allow the residual ethyl acetate to evaporate.

As in example I, to determine the effectiveness of this procedure at removing undesirable, non-polar impurities the pre- and post-extraction zinc citrate raw materials were prepared in aqueous solution and analyzed by immersion solid phase micro-extraction (SPME) GC-FID. The percent reduction of the undesirable materials from the commercially supplied material is set forth in Table 10, below.

TABLE 10

GC-FID analysis of zinc citrate raw material before and after LLE treatment with EtOAc.

| Zinc Citrate | Total Volatile Peak Area (GC/FID) | |
|---|---|---|
| | 1$^{st}$ Measurement | 2$^{nd}$ Measurement |
| Control (Pre-extract) | 14,754,990 | 11,517,257 |
| Post-extract | 3,467,513 | 3,198,938 |
| % Reduction | 74.6 | |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 g" is intended to mean "about 20 g." All percentages, ratios and proportions herein are on a weight basis unless otherwise indicated. Except as otherwise noted, all amounts including quantities, percentages, portions, and proportions, are not intended to indicate significant digits.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for improving the taste of oral care raw materials using solvent extraction, said process comprising the sequential steps of:
   a) first providing a solid oral care raw material composition selected from metal salts, sodium saccharin, metal oxides, rheology modifiers, structurants, fillers, abrasives, inorganic phosphates, salt dyes, and mixtures thereof wherein said oral care raw material composition comprises and one or more undesirable non-polar materials selected from residual alcohols, alcohol ethoxylates, aldehydes, ethers, ketones, alkylamines, amides and esters;
   b) then contacting said oral care raw material composition with an extraction solvent to form an extraction mixture comprising a solid phase and a solvent phase;
   c) then separating the solid phase from the extraction mixture; and
   d) then incorporating the solid phase into an oral care composition;
wherein the extraction solvent is selected from solvents having individual Hansen solubility parameters of a dispersion force component ($\delta_D$) ranging from about 13 to about 19 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

2. A process according to claim 1 wherein the extraction mixture further comprises from about 3% to about 90%, by weight of the composition, of water in an aqueous phase.

3. A process according to claim 1 wherein the oral care raw material is selected from zinc salts, sodium salts, potassium salts, calcium salts, magnesium salts, copper salts, zeolites, sodium saccharin, zinc oxide, titanium dioxide, cellulosic polymer rheology modifiers, polyethylene oxide, poloxamer, copolymers of acrylic acid crosslinked with a polyalkenyl polyether, maltodextrin, xanthan gum, and polyethylene glycols having a molecular weight of at least about 2000, calcium carbonate, silicas, pyrophosphates, sodium polyphosphates, cationic salt dyes, anionic salt dyes, and mixtures thereof.

4. A process according to claim 1 wherein the oral care raw material is a metal salt selected from sodium citrate, zinc citrate, stannous fluoride, stannous chloride, zinc lactate, calcium chloride, calcium carbonate, sodium hexametaphosphate, and mixtures thereof.

5. A process according to claim 1 wherein the oral care raw material is selected from stannous fluoride, copolymers of acrylic acid crosslinked with a polyalkenyl polyether, sodium acid pyrophosphate, zinc citrate, and mixtures thereof.

6. A process according to claim 1 wherein the step of separating the solid phase from the extraction mixture comprises passing the extraction mixture through a filter and collecting the solid material.

7. A process according to claim 1 wherein the extraction solvent has individual Hansen solubility parameters of a dispersion force component ($\delta_D$) ranging from about 13 to about 19 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$.

8. A process according to claim 1 wherein the extraction solvent is selected from ethyl acetate, water saturated ethyl acetate, ethyl propionate, ethyl butyrate, ethyl pentarioate, ethyl caproate, ethyl caprylate, ethyl pelargonate methyl acetate, methyl propionate, methyl butyrate, short chain esters, supercritical carbon dioxide, and mixtures thereof.

9. A process according to claim 1 wherein the extraction solvent is selected from food wade ethyl esters.

10. A process according to claim 9, wherein the extraction solvent is ethyl acetate.

11. A process according to claim 1 wherein the extraction mixture comprises from about 10% to about 90%, by weight of the mixture, of water; from about 5% to about 80%, by weight of the mixture, of oral care raw material; less than 10%, by weight of the oral care raw material, of undesirable non-polar impurities; and from about 10% to about 90%, by weight of the mixture, of solvent.

12. A process according to claim 1, wherein the ratio of extraction solvent to oral care raw material in the extraction mixture is from about 1:10 to about 10:1.

13. A process according to claim 2 wherein the step of separating the aqueous phase from the solvent phase further comprises centrifuging the extraction mixture.

14. A process according to claim 2 wherein the process further comprises mixing the extraction mixture for a period of from about 10 seconds to about one minute with vigorous mixing and at ambient temperature before allowing the mixture to settle into at least two phases and separating the aqueous phase from the solvent phase.

15. A process according to claim 2 wherein the process further comprises the step of removing any residual solvent from the aqueous phase wherein the step of removing any residual solvent from the aqueous phase includes the use of an industrial method selected from vacuum stripping (with or without heat), fractional distillation, wiped-film evaporator, carbon filtration, or combinations thereof.

16. A process according to claim 2 wherein the extraction mixture further comprises a phase separation enhancer selected from salt, pH modifiers, and mixtures thereof.

17. A process according to claim 1 for improving the taste of solid oral care raw materials using solvent extraction, said process comprising the sequential steps of:
   a) first providing said solid oral care raw material composition wherein said oral care raw material composition comprises:
      i) an orally acceptable raw material selected from stannous fluoride, silica, sodium saccharin, copolymers of acrylic acid crosslinked with a polyalkenyl polyether, sodium acid pyrophosphate, and mixtures thereof; and ii) one or more of said undesirable non-polar materials;
b) then contacting said oral care raw material composition with an extraction solvent to form an extraction mixture comprising a solid phase and a solvent phase; and
c) then separating the solid phase from the extraction mixture;

wherein the extraction solvent is selected from food grade ethyl esters and wherein the separated solid phase contains less than 2%, by weight, of said undesirable materials.

* * * * *